United States Patent
Asano

(10) Patent No.: US 9,734,997 B2
(45) Date of Patent: Aug. 15, 2017

(54) MASS SPECTROMETER AND MASS SPECTROMETRY METHOD

(71) Applicant: SHIMADZU CORPORATION, Kyoto-shi, Kyoto (JP)

(72) Inventor: Natsuyo Asano, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 15/105,081

(22) PCT Filed: Dec. 17, 2013

(86) PCT No.: PCT/JP2013/083702
§ 371 (c)(1),
(2) Date: Jun. 16, 2016

(87) PCT Pub. No.: WO2015/092862
PCT Pub. Date: Jun. 25, 2015

(65) Prior Publication Data
US 2016/0314949 A1    Oct. 27, 2016

(51) Int. Cl.
*H01J 49/00* (2006.01)
*G01N 30/72* (2006.01)
(Continued)

(52) U.S. Cl.
CPC ........ *H01J 49/005* (2013.01); *G01N 30/7266* (2013.01); *H01J 49/0031* (2013.01);
(Continued)

(58) Field of Classification Search
CPC .......... H01J 49/00; H01J 49/02; H01J 49/005; H01J 49/0072; H01J 49/06; H01J 49/062;
(Continued)

(56) References Cited

U.S. PATENT DOCUMENTS

2008/0283742 A1* 11/2008 Takeuchi .............. H01J 49/067
                                                                250/288
2009/0127453 A1*  5/2009 Ding ................... H01J 49/0072
                                                                250/282
(Continued)

FOREIGN PATENT DOCUMENTS

EP          2587521 A1    5/2013
JP        2002-525801 A   8/2002
(Continued)

OTHER PUBLICATIONS

Written Opinion for PCT/JP2013/083702 dated Feb. 4, 2014. [PCT/ISA/237].
(Continued)

*Primary Examiner* — Jason McCormack
(74) *Attorney, Agent, or Firm* — Sughrue Mion, PLLC

(57) ABSTRACT

The degree of ion dissociation which occurs within a first intermediate vacuum chamber (212) maintained at a comparatively low degree of vacuum depends not only on the amount of energy of the ion but also on the size and other properties of the ion. Accordingly, a predetermined optimum level of DC bias voltage is applied to an ion guide (24) so as to create, within the first intermediate vacuum chamber (212), a DC electric field which barely induces the dissociation of an ion originating from a target compound in a sample while promoting the dissociation of an ion originating from a foreign substance which will form a noise signal in the observation of the target compound. The optimum DC bias voltage is previously determined by creating extracted ion chromatograms based on data collected under various DC bias voltages and evaluating the SN ratio using the chromatograms. Consequently, the accuracy and sensitivity of the quantitative determination is improved as compared to a conventional system in which only the signal strength of the target compound is considered.

22 Claims, 3 Drawing Sheets

(51) Int. Cl.
 H01J 49/06 (2006.01)
 H01J 49/16 (2006.01)
(52) U.S. Cl.
 CPC ........ H01J 49/0045 (2013.01); H01J 49/063 (2013.01); H01J 49/165 (2013.01)
(58) Field of Classification Search
 CPC ...... H01J 49/063; H01J 49/065; H01J 49/066; H01J 49/068
 USPC ................ 250/281, 282, 283, 288, 290, 293
 See application file for complete search history.

(56) References Cited

U.S. PATENT DOCUMENTS

| | | | | |
|---|---|---|---|---|
| 2012/0056085 | A1* | 3/2012 | Giles | G01N 27/624 250/282 |
| 2015/0097114 | A1* | 4/2015 | Green | H01J 49/0059 250/282 |

FOREIGN PATENT DOCUMENTS

| | | |
|---|---|---|
| JP | 2004-514263 A | 5/2004 |
| WO | 00/16375 A1 | 3/2000 |
| WO | 02/44685 A2 | 6/2002 |
| WO | 2011/161788 A1 | 12/2011 |
| WO | 2012/108034 A1 | 8/2012 |
| WO | 2012/124020 A1 | 9/2012 |

OTHER PUBLICATIONS

International Search Report of PCT/JP2013/083702 dated Feb. 4, 2014.

Communication dated Dec. 20, 2016 from the Japanese Patent Office in counterpart Japanese application No. 2015-553258.

Communication dated Oct. 27, 2016, from the European Patent Office in counterpart European application No. 13899931.3.

* cited by examiner

MASS SPECTROMETER AND MASS SPECTROMETRY METHOD

CROSS REFERENCE TO RELATED APPLICATIONS

This application is a National Stage of International Application No. PCT/JP2013/083702 filed Dec. 17, 2013, the contents of all of which are incorporated herein by reference in their entirety.

TECHNICAL FIELD

The present invention relates to a mass spectrometer and mass spectrometry method, and more specifically, to a mass spectrometer and mass spectrometry method suitable for a liquid chromatograph mass spectrometer including a liquid chromatograph (LC) combined with a mass spectrometer. The term "mass spectrometer" includes a mass spectrometer capable of an MS/MS analysis, such as a tandem quadrupole mass spectrometer.

BACKGROUND ART

In general, a quantitative analysis of a target component in a sample using a liquid chromatograph mass spectrometer (LC-MS) is performed as follows: A selective ion monitoring (SIM) measurement or multiple reaction monitoring (MRM) measurement for a mass-to-charge ratio corresponding to an ion originating from the target component is performed within the vicinity of the retention time at which the target component is eluted. Based on the data obtained by the measurement, an extracted ion chromatogram is created. In this extracted ion chromatogram, the area value of the peak corresponding to the target component is calculated. Eventually, the amount or concentration of the target component is calculated from the peak area value using a calibration curve previously created.

In an atmospheric pressure ionization mass spectrometer which is used in a liquid chromatograph mass spectrometer, the generation efficiency and passage efficiency of ions change depending on various control parameters, such as the voltage applied to an ion transport optical system (which is called the "ion lens", "ion guide" or otherwise), the temperature of the ionization probe in the atmospheric pressure ion source and that of the heated capillary for transporting ions. The optimum values of those control parameters with which the highest levels of ion generation efficiency and ion passage efficiency can be achieved also depend on the mass-to-charge ratio of the ion originating from the target component to be analyzed. Therefore, in order to enhance the accuracy of the quantitative determination for the target component or to improve the lower limit of the quantitative determination (i.e. to decrease the lower limit), it is necessary to set the various aforementioned control parameters at their respective optimum values according to the target component to be analyzed when the measurement is performed. Accordingly, conventional mass spectrometers are provided with the automatic tuning function for automatically searching for the optimum values of the control parameters for each target component beforehand (i.e. in advance of the measurement of the target sample).

As described in Patent Literatures 1, 2 or other documents, the automatic tuning is normally achieved by actually performing a measurement of a target component in a sample while changing the value of the control parameter and by automatically processing the thereby obtained measurement result. When a sample which only contains the target component is used as the sample, an infusion method or flow injection method is normally used to introduce the sample into the mass spectrometer. When a sample which contains a plurality of components in addition to the target component is used, a sample that contains the components which have been separated by a column is introduced into the mass spectrometer.

The primary reason for performing the automatic tuning is to detect a trace amount of component with a high level of sensitivity. Accordingly, in normal situations, the parameter values for controlling each section of the system are adjusted so as to maximize the signal strength of the ion originating from the target component. However, conducting a measurement under the control parameters adjusted in this manner does not always ensure that the highest level of quantitative accuracy and sensitivity is achieved. The reason is as follows: If the background noise within the time range where the target component is eluted is increased due to a foreign substance or other factors, the SN ratio may become lower than the highest possible level even when the signal strength of the ion originating from the target component is maximized. In such a case, the accuracy of the peak area value in the extracted ion chromatogram will be low.

CITATION LIST

Patent Literature

Patent Literature 1: WO 2012/108034 A
Patent Literature 2: WO 2012/124020 A

SUMMARY OF INVENTION

Technical Problem

Therefore, the conventional automatic tuning method used in the liquid chromatograph mass spectrometer does not always ensure that the control parameters are set so that the accuracy and sensitivity of the quantitative determination reaches the highest possible level. In this respect, there is room for improving the quantitative accuracy and sensitivity. The present invention has been developed in view of such a problem. Its objective is to provide a mass spectrometer and mass spectrometry method capable of more correctly setting the control parameters in the mass spectrometer for each kind of target component so that the accuracy, lower limit and other elements of the quantitative determination will be higher or better than the conventional levels.

Solution to Problem

In an atmospheric pressure ionization mass spectrometer using an electrospray ion source or similar ion source, the configuration of the so-called "multistage differential pumping system" is often used to maintain a high degree of vacuum atmosphere within the analysis chamber which contains the mass spectrometer section including a quadrupole mass filter. In such a mass spectrometer, a high concentration of residual gas is present within the intermediate vacuum chamber located in the next stage from the ionization chamber. Therefore, an ion having a certain amount of energy easily collides with the residual gas in this intermediate vacuum chamber and becomes dissociated due to the collision induced dissociation process. The ease of occurrence of this dissociation depends not only on the amount of energy which the ion possesses but also on the ease of collision with the residual gas. Accordingly, for example, ions having almost equal mass-to-charge ratios have different probabilities of undergoing the collision induced dissociation if they have different sizes due to a difference in their compositions or three-dimensional structures. Normally, two different kinds of ions which are identical or close to each other in mass-to-charge ratio cannot be separated from each other in the mass spectrometer section. However, if one of the ions is dissociated within the first intermediate vacuum chamber, it is possible to separate those ions in the mass spectrometer section.

To cause the collision induced dissociation in the previously described manner, it is necessary to impart more than a certain amount of energy to the ions before making them collide with the residual gas. Therefore, by controlling the strength of the DC electric field within the first intermediate vacuum chamber, it is possible to regulate the ease of occurrence of the collision induced dissociation for different kinds of ions having different sizes or other properties. Such a principle is utilized in the mass spectrometer and mass spectrometry method according to the present invention: The DC electric field within the first intermediate vacuum chamber is set so that an ion originating from the target component to be observed will be allowed to pass through the first intermediate vacuum chamber with the lowest amount of dissociation while an ion originating from a foreign substance which may possibly form a noise signal in the observation of the target component will undergo dissociation with the highest possible efficiency.

That is to say, the mass spectrometer according to the present invention developed for solving the previously described problem is a mass spectrometer including: an ionization chamber for ionizing a component in a sample in an ambience of atmosphere pressure; an analysis chamber maintained at a high degree of vacuum containing a mass spectrometry section for detecting the ions according to their mass-to-charge ratios; one or a plurality of intermediate vacuum chambers provided between the ionization chamber and the analysis chamber; an ion introduction section with an opening for introducing ions from the ionization chamber into the subsequently located first intermediate vacuum chamber; and an ion transport section having an opening for introducing ions from the first intermediate chamber into the intermediate vacuum chamber or the analysis chamber in the next stage, the mass spectrometer including:

a) an ion guide, placed within the first intermediate vacuum chamber, for creating a radio-frequency electric field for converging ions introduced through the ion introduction section to the first intermediate vacuum chamber while transporting the ions through the ion transport section to the subsequent stage; and b) a voltage generator for applying a DC voltage to at least one of the three elements of the ion introduction section, the ion guide and the ion transport section, with the DC voltage adjusted so as to create a DC electric field within the first intermediate vacuum chamber so that the efficiency of the collision induced dissociation for an ion originating from at least one foreign component within the first intermediate vacuum chamber is higher than the efficiency of the collision induced dissociation for an ion originating from a target component.

The mass spectrometry method according to the present invention developed for solving the previously described problem is a method for mass spectrometry using a mass spectrometer including: an ionization chamber for ionizing a component in a sample in an ambience of atmosphere pressure; an analysis chamber maintained at a high degree of vacuum containing a mass spectrometry section for detecting ions after separating the ions according to their mass-to-charge ratios; one or a plurality of intermediate vacuum chambers provided between the ionization chamber and the analysis chamber; an ion introduction section with an opening for introducing ions from the ionization chamber into the subsequently located first intermediate vacuum chamber; an ion transport section having an opening for introducing ions from the first intermediate chamber into the intermediate vacuum chamber or the analysis chamber in the next stage; and an ion guide, placed within the first intermediate vacuum chamber, for creating a radio-frequency electric field for converging ions introduced through the ion introduction section to the first intermediate vacuum chamber while transporting the ions through the ion transport section to the subsequent stage, the method characterized by:

applying a predetermined DC voltage to at least one of the three elements of the ion introduction section, the ion guide and the ion transport section, so as to create, within the first intermediate vacuum chamber, a DC electric field which induces a dissociation of an ion due to collision induced dissociation within the first intermediate vacuum chamber, with the value of the DC voltage adjusted, using a variation in the ease of occurrence of the collision induced dissociation depending on the kind of component, so as to increase the SN ratio of the detection signal for an ion originating from a target component.

For example, the mass spectrometer according to the present invention is an atmospheric pressure ionization mass spectrometer using an atmospheric pressure ionization method, such as electrospray ionization (ESI), atmospheric pressure chemical ionization (APCI) or atmospheric pressure photoionization (APPI). Examples of the ion introduction section or ion transport section include a cylindrical pipe or skimmer having an opening through which ions can pass. The ion guide may have any of the various conventionally known structures.

In the mass spectrometer and mass spectrometry method according to the present invention, the ion introduction section, ion guide and ion transport section are placed within the first intermediate vacuum chamber, with DC voltages applied to these units so as to create a DC electric field for accelerating or decelerating ions within the first intermediate vacuum chamber. By appropriately adjusting the value of the DC voltage applied to at least one of these units, a DC electric field is created in which the efficiency of the collision induced dissociation for an ion originating from at least one foreign component is higher than the efficiency of the collision induced dissociation for an ion originating from a target component. The phase "an ion originating from at least one foreign component" means an ion originating from at least one foreign component which is impossible or difficult to be separated from the ion originating from the target component by the mass spectrometer section in the subsequent stage. Due to the effect of the DC electric field, the ion originating from the foreign component which may possibly form a noise signal in the observation of the target component is made to undergo collision induced dissociation within the first intermediate vacuum chamber and be broken into ions having smaller mass-to-charge ratios, to be eventually removed in the mass spectrometer section. Consequently, an amount of ions containing the ion originating from the target component with a high level of purity arrive at the ion detector, so that the SN ratio of the detection signal improves.

When the strength of a portion of the DC electric field formed within the first intermediate vacuum chamber changes, the ease of occurrence of the collision induced dissociation for each different kind of ion also changes. Accordingly, the voltage generator may be configured so as to adjust the ease of occurrence of the collision induced dissociation within the first intermediate vacuum chamber by changing the DC voltage applied to one of the three elements of the ion introduction section, the ion guide and the ion transport section while maintaining the DC voltages applied to the other two elements. Needless to say, it is also possible to adjust the ease of occurrence of the collision induced dissociation within the first intermediate vacuum chamber by changing the DC voltages applied to two or more of the three elements of the ion introduction section, the ion guide and the ion transport section.

Preferably, the mass spectrometer according to the present invention should further include an optimum voltage searcher for searching for an optimum voltage that is a value of the DC voltage at which the detection signal of the ion originating from the target component has an optimum or approximately optimum SN ratio.

In this configuration, the optimum voltage searcher may include:

a search process controller for controlling the voltage generator so as to change the value of the DC voltage in a stepwise manner; and an SN ratio comparator for acquiring a detection signal for the ion originating from the target component every time the value of the DC voltage is changed in the stepwise manner under the control of the search process controller, for calculating the SN ratio of the detection signal acquired under each different value of the DC voltage, and for comparing the calculated SN ratios.

The mass spectrometer according to the present invention may further include:

a storage section for storing information related to the optimum voltage obtained by the optimum voltage searcher; and a measurement process controller for controlling the voltage generator during a measurement process for the target component in a sample so that the optimum voltage is applied to at least one of the three elements of the ion introduction section, the ion guide and the ion transport section based on the information stored in the storage section.

The SN ratio of the detection signal for the ion originating from the target component can be calculated by a conventionally known method. For example, when a chromatogram showing a temporal change in the detection signal for the ion originating from the target component can be created, the signal intensity at the peak top of a peak corresponding to the target component in the chromatogram can be used as "S" while an average of the signal intensity over a time range outside the peak period (the time range from the beginning point to the ending point of the peak) can be used as "N" to calculate the SN ratio.

For example, in a liquid chromatograph mass spectrometer, the state of elution of the target or foreign compounds changes according to the conditions of the chromatographic separation and other factors. The system having the previously described configuration can determine an appropriate value of the DC voltage corresponding to the conditions of the chromatographic separation and other factors during the measurement process, so that the SN ratio for the target component can be specifically maximized.

The mass spectrometer according to the present invention may preferably be configured so that:

the storage section holds information related to the optimum voltage for each component; and the measurement process controller retrieves, from the storage section, a piece of information related to the optimum voltage according to the kind of the component to be analyzed, and controls the voltage generator based on the information.

In the case where the mass spectrometer according to the present intention is a mass spectrometer in which a sample separated into components by a column of a chromatograph is introduced into an ionization probe placed within the ionization chamber to perform a mass spectrometry, the measurement process controller may preferably be configured to control the voltage generator during the measurement process so as to change the optimum voltage for each component contained in the introduced sample based on the information stored in the storage section.

According to this configuration, when a plurality of target components is contained in the sample, the SN ratio of the detection signal is maximized for each target component. Consequently, the quantity of any of those components can be determined at a high level of accuracy and sensitivity.

Advantageous Effects of the Invention

With the mass spectrometer and mass spectrometry method according to the present invention, the SN ratio of the detection signal for a target component in a sample improves. Therefore, for example, it is possible to improve the accuracy and sensitivity of a quantitative analysis based on a chromatogram corresponding to the target compound. Consequently, it becomes possible to determine the quantity of a trace amount of component which could not have been detected by conventional methods.

DESCRIPTION OF EMBODIMENTS

Figure 1:
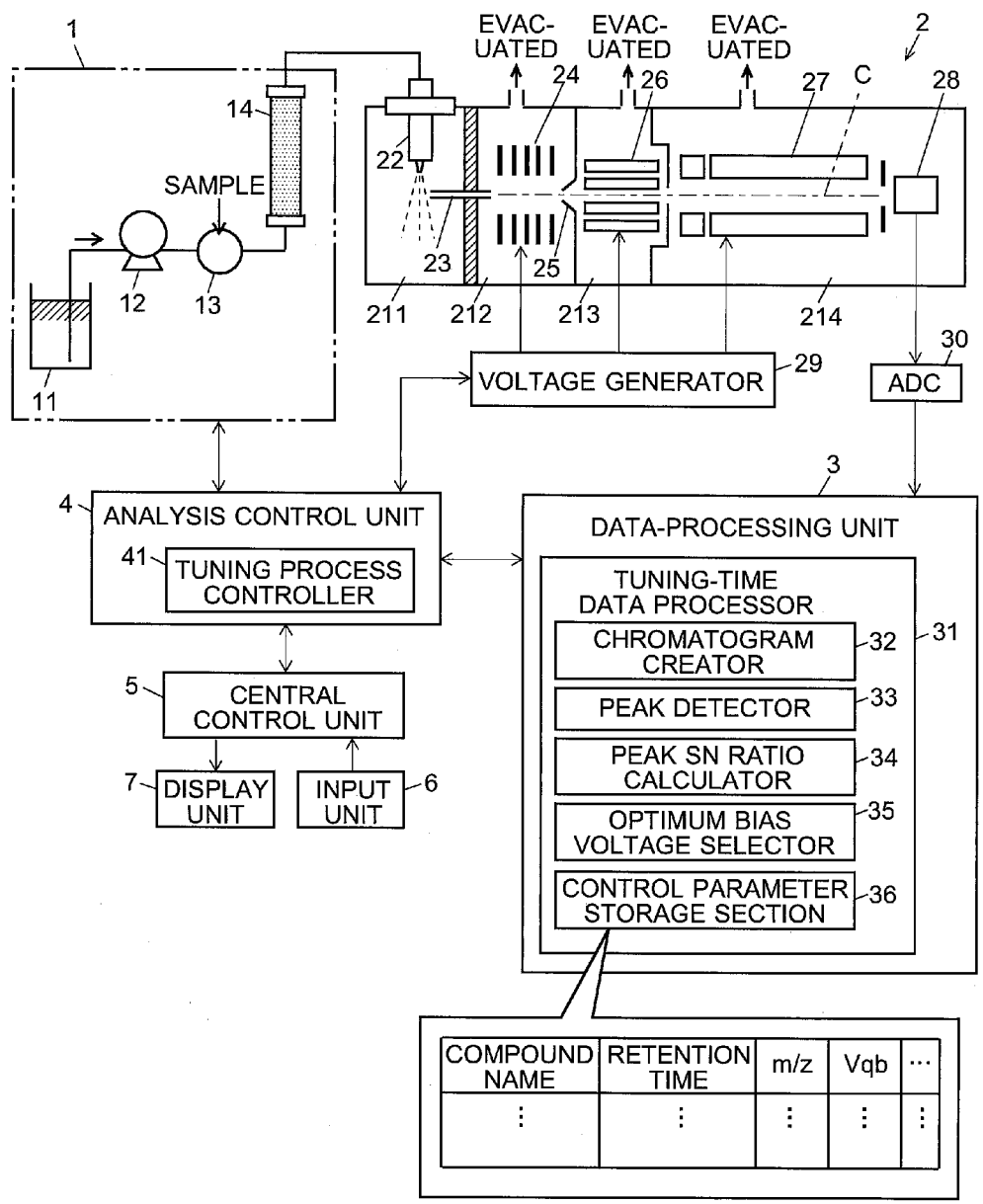
FIG. 1 is a configuration diagram showing the main components of an LC-MS as one embodiment of the present invention.

One embodiment of the liquid chromatograph mass spectrometer (LC-MS) which includes a mass spectrometer according to the present invention is hereinafter described with reference to the attached drawings. FIG. 1 is a configuration diagram showing the main components of the LC-MS of the present embodiment.

The liquid chromatograph unit 1 includes a mobile-phase container 11, pump 12, injector 13 and column 14. In this liquid chromatograph unit 1, the pump 12 draws a mobile phase from the mobile-phase container 11 and supplies it to the column 14 at a fixed flow rate. The injector 13 injects a fixed amount of sample into the mobile phase at a predetermined timing. The injected sample is carried into the column 14 by the stream of the mobile phase. While the sample is passing through this column 14, the compounds (sample components) contained in the sample are separated, to be eventually eluted from the exit port of the column 14 in a temporally separated form.

The mass spectrometer unit 2, which functions as the detector for the liquid chromatograph unit 1, has the configuration of a multistage differential pumping system having an ionization chamber 211 maintained at substantially atmospheric pressure and an analysis chamber 214 evacuated to a high degree of vacuum by a high-performance vacuum pump (not shown), between which first and second intermediate vacuum chambers 212 and 213 are provided having their degrees of vacuum increased in a stepwise manner. The ionization chamber 211 is provided with an electrospray ionization (ESI) probe 22 for spraying a sample solution while giving electric charges to this solution. The ionization chamber 211 communicates with the first intermediate vacuum chamber 212 in the next stage through a thin heated capillary 23 (which corresponds to the ion introduction section in the present invention). The first and second intermediate vacuum chambers 212 and 213 are separated from each other by a skimmer 25 (which corresponds to the ion transport section in the present invention) having a small hole at its apex. Ion guides 24 and 26 for converging ions while transporting them to the subsequent section are provided in the first and second intermediate vacuum chambers 212 and 213, respectively. Within the analysis chamber 214, a quadrupole mass filter 27 for separating ions according to their mass-to-charge ratios and an ion detector 28 are placed.

In the mass spectrometer unit 2, when the eluate from the exit port of the column 14 reaches the ESI ionization probe 22, a sample solution with electric charges given from the tip of the probe 22 is sprayed. The sprayed droplets with electric charges are divided into smaller sizes due to the electrostatic force. During this process, ions originating from the compounds in the sample are produced. Those ions are sent through the heated capillary 23 into the first intermediate vacuum chamber 212, where the ions are converged by the ion guide 24 and sent through the small hole at the apex of the skimmer 25 into the second intermediate vacuum chamber 213. These ions are forwarded through the ion guide 26 into the analysis chamber 214, where they are introduced into the space extending along the longitudinal axis of the quadrupole mass filter 27. It should be noted that the ionization method used within the ionization chamber 211 is not limited to the ESI but may be performed using a different atmospheric pressure ionization method, such as the APCI or APPI.

A voltage generator 29 applies a predetermined form of voltage to each of the four rod electrodes forming the quadrupole mass filter 27. Only an ion having a specific mass-to-charge ratio m/z corresponding to that voltage is allowed to pass through the quadrupole mass filter 27 and reach the ion detector 28. The ion detector 28 produces detection signals corresponding to the amount of ions it has received. The detection signals are converted into digital data in the analogue-to-digital converter (ADC) 30 and fed to a data-processing unit 3.

The data-processing unit 3 includes a tuning-time data processor 31 as its functional block. The tuning-time data processor 31 includes a chromatogram creator 32, peak detector 33, peak SN ratio calculator 34, optimum bias voltage selector 35 and control parameter storage section 36 as its functional blocks. The analysis control unit 4, which controls each section of the system, includes a tuning process controller 41 as its functional block. A central control unit 5, which is equipped with an input unit 6 and display unit 7, generally controls the input-output interface and the entire system.

At least a portion of the functions of the central control unit 5, analysis control unit 4, data-processing unit 3 and other units can be realized using a multipurpose personal computer as the hardware resource by running, on this computer, a dedicated controlling and processing software program previously installed on the same computer.

Figure 2:
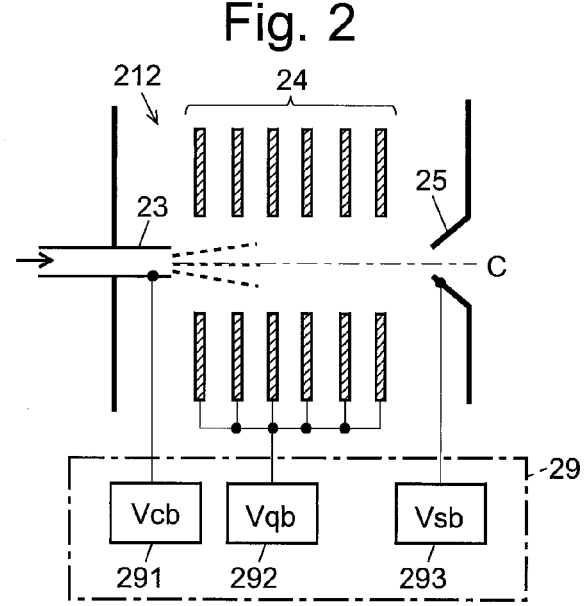
FIG. 2 is a configuration diagram concerned with the components within the first intermediate vacuum chamber in the LC-MS of the present embodiment.

FIG. 2 is a schematic configuration diagram concerned with the components placed within the first intermediate vacuum chamber 212.

The ion guide 24 includes four virtual rod electrodes arranged around the ion beam axis C, with each virtual rod electrode consisting of a plurality of plate electrodes arrayed along the ion beam axis C. The two sets of plate electrodes which are respectively included the two virtual rod electrodes neighboring each other around the ion beam axis C are supplied with radio-frequency voltages having the same amplitude and frequency with a phase difference of 180 degrees. The applied voltages create a quadrupole radio-frequency electric field within the space surrounded by the four virtual rod electrodes. Due to the effect of this electric field, the ions are converged into the vicinity of the ion beam axis C while being transported. This is a commonly known function of the ion guide in a conventional mass spectrometer, examples of which are disclosed in Patent Literature 1 or 2.

In the LC-MS of the present embodiment, in addition to those radio-frequency voltages, a predetermined level of DC bias voltage Vqb is applied from the second DC voltage source 292 included in the voltage generator 29 to the plate electrodes constituting the ion guide 24. Additionally, another predetermined level of DC bias voltage Vcb is applied from the first DC voltage source 291 to the heated capillary 23, and still another predetermined level of DC bias voltage Vsb is applied from the third DC voltage source 293 to the skimmer 25. The DC bias voltages Vcb, Vqb and Vsb respectively applied to the heated capillary 23, ion guide 24 and skimmer 25 create a DC electric field within the first intermediate vacuum chamber 212. Depending on the voltage values of the DC bias voltages Vcb, Vqb and Vsb, the DC electric field becomes either an accelerating field which accelerates ions or a decelerating field which decelerates ions.

Although the first intermediate vacuum chamber 212 is evacuated, the degree of vacuum is low and a considerable amount of residual gas is present, due to the continuous inflow of gas (air) from the ionization chamber 211 through the heated capillary 23. If an ion introduced into the first intermediate vacuum chamber 212 collides with the residual gas while having a certain amount of energy, the ion is broken into fragments due to a similar effect to the collision induced dissociation (CID). This process is called the "in-source decay", although it is not a process which occurs within the ion source. The ease of occurrence of the in-source decay depends on the amount of energy which the ion possesses. Accordingly, if the strength of the DC electric field formed within the first intermediate vacuum chamber 212 is changed, the efficiency of the in-source decay also changes. The ease of occurrence of the in-source decay also depends on the mass-to-charge ratio, size and other properties of the ion. Therefore, for example, a specific combination of the DC bias voltages Vcb, Vqb and Vsb respectively applied to the heated capillary 23, ion guide 24 and skimmer 25 can create a situation in which an ion originating from one compound easily undergoes the in-source decay while an ion originating from another compound does not easily undergo the in-source decay.

In the LC-MS of the present embodiment, such a difference in the ease of occurrence of the in-source decay is utilized to reduce the amount of noise due to a foreign compound. This is achieved by decreasing the likelihood of the dissociation of an ion originating from a target compound to be observed, while promoting the dissociation of an ion originating from a different compound (foreign substance) which is close (or identical) to the ion originating from the target compound in terms of the mass-to-charge ratio and therefore cannot be sufficiently separated from the latter ion by the quadrupole mass filter 27.

Figure 3:
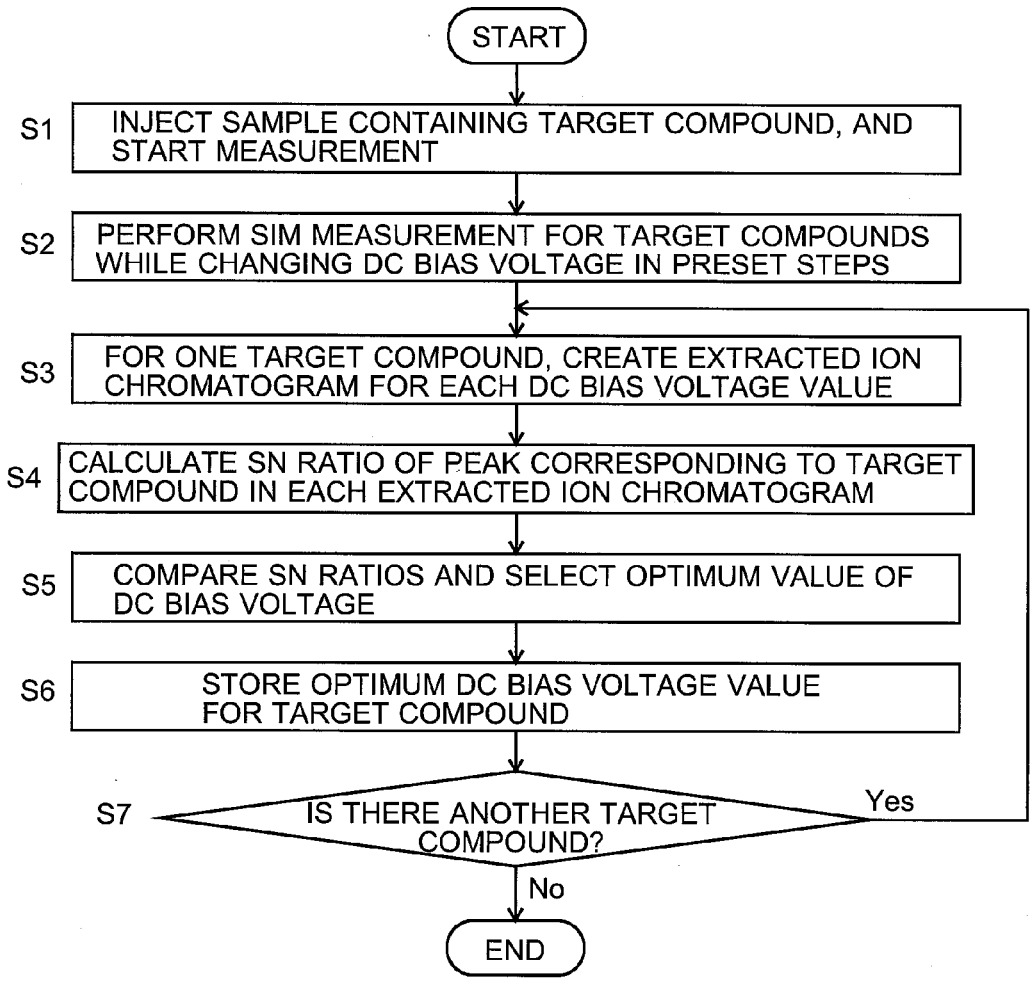
FIG. 3 is a flowchart of the tuning operation for searching for an optimum level of the DC bias voltage for the ion guide in the LC-MS of the present embodiment.
Figure 4:
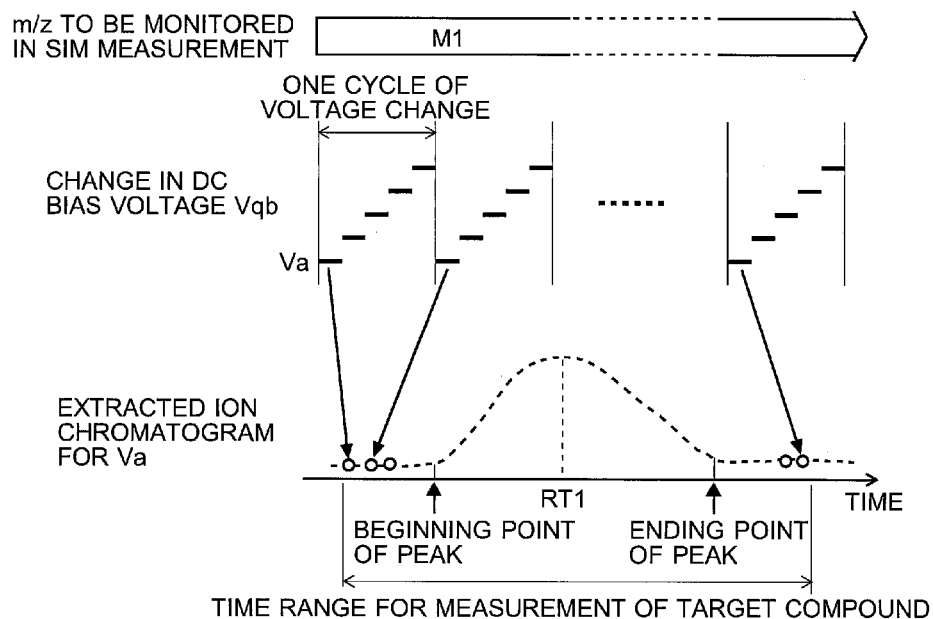
FIG. 4 is a conceptual diagram for explaining the tuning operation shown in FIG. 3.

Next, the data processing and controlling operation during the tuning process for searching for an optimum level of the DC bias voltage for the ion guide in the LC-MS of the present embodiment is described with reference to FIGS. 3 and 4. FIG. 3 is a flowchart of the tuning operation in the LC-MS of the present embodiment. FIG. 4 is a conceptual diagram for explaining the same tuning operation.

In the present example, a sample containing a plurality of target compounds is used in the tuning process. It is also possible to perform the tuning process using a sample containing a single kind of target compound at a high degree of purity. In that case, it is unnecessary to separate compounds using the column 14, so the column 14 can be removed and the sample can be introduced by a flow injection method or infusion method.

When a command for executing the optimization process for the DC bias voltage Vqb applied to the ion guide 24 is issued, a predetermined sample is injected from the injector 13 into the mobile phase under the control of the tuning process controller 41, and the measurement is initiated (Step S1). The tuning process controller 41 controls each section of the mass spectrometer unit 2 so as to perform an SIM measurement for monitoring the mass-to-charge ratio of an ion originating from a target compound within a predetermined period of time including the retention time of that target compound. It also controls the voltage generator 29 during this SIM measurement so that the DC bias voltage Vqb applied to the ion guide 24 is changed within a predetermined voltage range in predetermined steps of voltage.

In the example shown in FIG. 4, the DC bias voltage Vqb is sequentially set at five levels during the SIM measurement for the ion having a mass-to-charge ratio (m/z) of M1. It is naturally possible to change the DC bias voltage Vqb in smaller steps with a greater number of levels. Such a process of changing the DC bias voltage Vqb is repeated as shown in FIG. 4. Accordingly, within the time range of the measurement for one target compound, the signal strength data for the ion having the mass-to-charge ratio (m/z) of M1 are repeatedly obtained at each value of the DC bias voltage. If there are a plurality of target compounds, a similar measurement is performed for each compound at the timing where that compound is eluted (Step S2).

After the measurement is completed, the chromatogram creator 32 in the tuning-time data processor 31 creates an extracted ion chromatogram for each value of the DC bias voltage based on the data collected through the SIM measurement (Step S3). In the example shown in FIG. 4, since the DC bias voltage is set at five levels, five extracted ion chromatograms are created per one target compound. In normal situations, a peak corresponding to the ion originating from the target compound should be present in any of these extracted ion chromatograms.

As described earlier, if an ion introduced through the heated capillary 23 into the first intermediate vacuum chamber 212 collides with the residual gas while having a considerable amount of energy, the ion is broken into fragments due to the in-source decay. The ion originating from the target compound and the ion originating from a foreign substance can both undergo fragmentation due to the in-source decay. However, the energy dependency of the efficiency of the in-source decay changes from ion to ion. Therefore, when the DC bias voltage is set at a certain value, the ion originating from the target compound is less likely to undergo the in-source decay while the ion originating from the foreign substance frequently undergoes the in-source decay. Even when the mass-to-charge ratio of the ion originating from the foreign substance is initially the same as or extremely close to that of the ion originating from the target compound, if the ion originating from the foreign substance is broken into fragments due to the in-source decay, the mass-to-charge ratio of the ion changes (normally, to a smaller value) and it becomes possible to separate the ion from the target ion by the quadrupole mass filter 27. Consequently, the selectivity for the ion originating from the target compound improves. Even when a portion of the ion originating from the target compound is broken into fragments due to the in-source decay and disallowed to pass through the quantitative mass filter 27, if its degree of fragmentation is lower than that of the ion originating from the foreign substance, the SN ratio of the detection signal for the ion originating from the target compound will improve. Accordingly, the peak detector 33 detects the peak corresponding to the target compound in each of the extracted ion chromatograms corresponding to the different values of the DC bias voltage, and the peak SN ratio calculator 34 computes the SN ratio of the detected peak (Step S4).

The SN ratio of the peak may be calculated by any method which has been commonly used to calculate the SN ratio of a peak on a chromatogram. For example, the signal intensity at the peak top of the peak corresponding to the target component can be used as "S" of the SN ratio. "N" of the SN ratio can be calculated using the signal values obtained within the periods of time $\pm \Delta T$ arbitrarily set before and after the point in time where the target compound is eluted (retention time), exclusive of the peak section of the target compound (the time range from the beginning point to the ending point of the peak), where $\Delta T$ satisfies $0 < \Delta T \leq Te - Te$, with Ts representing the measurement starting time and Te representing the measurement finishing time; for example, an average of these signal values can be used as "N". To allow for such a calculation of the SN ratio, the SIM measurement for one target compound should preferably be performed over a time range which covers a sufficient length of time around the retention time of the target compound so that a period of time with no elution of the target compound will be included.

After the peak SN ratio for one target compound in each of the plurality of extracted ion chromatograms created for that target compound has been calculated, the optimum bias voltage selector 35 compares those peak SN ratios and selects the DC bias voltage which gives the highest peak SN ratio (Step S5). This selected voltage value is the optimum DC bias voltage corresponding to the target component concerned. Accordingly, this optimum value of the DC bias voltage is related to that target compound and stored in the control parameter storage section 36 (Step S6). It is also possible to store the optimum value of the DC bias voltage along with the retention time and mass-to-charge ratio for the same target compound, as shown in FIG. 1.

Subsequently, it is determined whether or not there is another target component for which the optimum DC bias voltage has not yet been determined (Step S7). If there is another target compound, the operation returns to Step S3 to repeat the processes of Steps S3 through S6. When the optimum DC bias voltage has been obtained for all target compounds contained in the sample ("No" in Step S7), the tuning process for searching for the optimum DC bias voltage for the ion guide 24 is completed. As a result of such a process, the optimum value of the DC bias voltage is stored for each of the plurality of compounds in the control parameter storage section 36.

When a quantitative analysis for a known target compound is performed with the LC-MS of the present embodiment, the operator using the input unit 6 initially sets the kind of target compound to be analyzed. After specifying other necessary measurement conditions, the operator commands the system to begin the measurement. Then, a prepared sample containing the target compound is injected from the injector 13 into the mobile phase. An SIM measurement for monitoring the mass-to-charge ratio corresponding to the target component is performed within a preset time range including the retention time of the target compound. During this measurement, the analysis control unit 4 controls the voltage generator 29 so that the DC bias voltage corresponding to the target compound read from the control parameter storage section 36 is applied to the ion guide 24. Consequently, the SIM measurement is performed under such a condition that the SN ratio of the peak corresponding to the target component is maximized. An extracted ion chromatogram created from the data obtained in this manner has a reduced noise level superposed on the peak corresponding to the target compound. Therefore, the peak area value will be more accurately calculated and the quantitative accuracy will be improved.

Figure 5A:
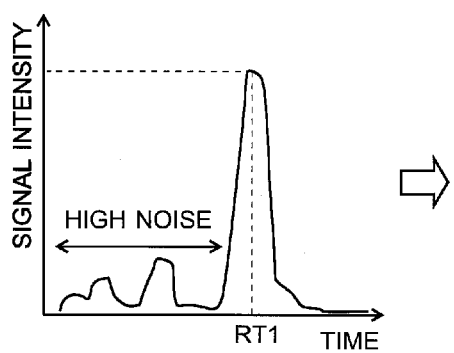
FIGS. 5A and 5B are diagrams showing chromatograms for explaining the effect obtained when the DC bias voltage optimization for the ion guide is performed.
Figure 5B:
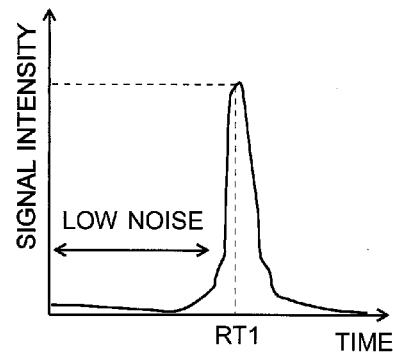

FIGS. 5A and 5B show a comparison of the extracted ion chromatograms, where FIG. 5A is the case where no DC bias voltage is applied to the ion guide 24, and FIG. 5B is the case where the optimized DC bias voltage is applied. As can be seen in FIGS. 5A and 5B, when an in-source decay is induced by applying an appropriate level of DC bias voltage to the ion guide 24, the level of the noise superposed on the peak originating from the target component having retention time RT1 decreases. Although the signal strength of the peak originating from the target component also slightly decreases, the SN ratio of the peak originating from the target component improves because the noise level is decreased by a greater amount. Consequently, the accuracy of the area value of this peak improves.

In a quantitative analysis of a plurality of target compounds contained in a sample, the DC bias voltage applied to the ion guide 24 is changed for each range of time within which one target compound is eluted. By this operation, a high level of quantitative determination is realized for any of the compounds contained in the sample.

In the previous embodiment, the result of the tuning process is stored in the control parameter storage section 36, and the DC bias voltage value stored in the control parameter storage section 36 is automatically set as an analysis condition when a measurement for a sample containing the same compound is performed. Alternatively, the extracted ion chromatograms obtained in the previously described tuning process may be used for the quantitative determination of the target compound as follows: Among the plurality of extracted ion chromatograms obtained under different values of the DC bias voltage, the extracted ion chromatogram obtained under the DC bias voltage value which gives the highest peak SN ratio is selected. In this extracted ion chromatogram, the area value of the peak corresponding to the target compound is calculated, and the quantitative value of the target compound is calculated from this peak area value.

The mass spectrometer in the previous embodiment is a mass spectrometer using a single type quadrupole mass filter. It is evident that a tandem quadrupole mass spectrometer can also be used. In that case, the selectivity for the ion originating from the target compound can be further improved by performing an MRM measurement instead of the SIM measurement.

The previous embodiment is one example of the present invention, and any change, addition or modification appropriately made within the spirit of the present invention in any respect other than the previously described ones will evidently fall within the scope of claims of the present application.

REFERENCE SIGNS LIST

1 . . . Liquid Chromatograph Unit
11 . . . Mobile-Phase Container
12 . . . Pump
13 . . . Injector
14 . . . Column Tube
2 . . . Mass Spectrometer Unit
211 . . . Ionization Chamber
212, 213 . . . Intermediate Vacuum Chamber
214 . . . Analysis Chamber
22 . . . Ionization Probe
23 . . . Heated Capillary
24 . . . Ion Guide
25 . . . Skimmer
26 . . . Multipole Ion Guide
27 . . . Quadrupole Mass Filter
28 . . . Detector
29 . . . Voltage Generator
30 . . . Analogue-To-Digital Converter
3 . . . Data-Processing Unit
31 . . . Tuning-Time Data Processor
32 . . . Chromatogram Creator
33 . . . Peak Detector
34 . . . Peak SN Ratio Calculator
35 . . . Optimum Bias Voltage Selector
36 . . . Control Parameter Storage Section
4 . . . Analysis Control Unit
41 . . . Tuning Process Controller
5 . . . Central Control Unit
6 . . . Input Unit
7 . . . Display Unit

The invention claimed is:

1. A mass spectrometer, comprising:
an ionization chamber for ionizing a component in a sample in an ambience of atmosphere pressure;
an analysis chamber maintained at a high degree of vacuum containing a mass spectrometry section for detecting ions after separating the ions according to their mass-to-charge ratios; one or a plurality of intermediate vacuum chambers provided between the ionization chamber and the analysis chamber;
an ion introduction section with an opening for introducing ions from the ionization chamber into the subsequently located first intermediate vacuum chamber;

an ion transport section having an opening for introducing ions from the first intermediate chamber into the intermediate vacuum chamber or the analysis chamber in a next stage;

an ion guide, placed within the first intermediate vacuum chamber, for creating a radio-frequency electric field for converging ions introduced through the ion introduction section to the first intermediate vacuum chamber while transporting the ions through the ion transport section to the subsequent stage; and a voltage generator for applying a DC voltage to at least one of three elements of the ion introduction section, the ion guide and the ion transport section, with the DC voltage adjusted so as to create a DC electric field within the first intermediate vacuum chamber so that an efficiency of collision induced dissociation for an ion originating from at least one foreign component within the first intermediate vacuum chamber is higher than the efficiency of the collision induced dissociation for an ion originating from a target component.

2. The mass spectrometer according to claim 1, further comprising:

an optimum voltage searcher for searching for an optimum voltage that is a value of the DC voltage at which a detection signal of the ion originating from the target component has an optimum or approximately optimum SN ratio.

3. The mass spectrometer according to claim 2, wherein: the optimum voltage searcher comprises:

a search process controller for controlling the voltage generator so as to change the value of the DC voltage in a stepwise manner; and an SN ratio comparator for acquiring a detection signal for the ion originating from the target component every time the value of the DC voltage is changed in the stepwise manner under the control of the search process controller, for calculating the SN ratio of the detection signal acquired under each different value of the DC voltage, and for comparing the calculated SN ratios.

4. The mass spectrometer according to claim 2, further comprising:

a storage section for storing information related to the optimum voltage obtained by the optimum voltage searcher; and a measurement process controller for controlling the voltage generator during a measurement process for the target component in a sample so that the optimum voltage is applied to at least one of the three elements of the ion introduction section, the ion guide and the ion transport section based on the information stored in the storage section.

5. The mass spectrometer according to claim 4, wherein: the storage section holds information related to the optimum voltage for each component; and the measurement process controller retrieves, from the storage section, a piece of information related to the optimum voltage according to a kind of the component to be analyzed, and controls the voltage generator based on the information.

6. The mass spectrometer according to claim 5, wherein: the mass spectrometer is a mass spectrometer in which a sample separated into components by a column of a chromatograph is introduced into an ionization probe placed within the ionization chamber to perform a mass spectrometry; and the measurement process controller controls the voltage generator during the measurement process so as to change the optimum voltage for each component contained in the introduced sample based on the information stored in the storage section.

7. The mass spectrometer according to claim 1, wherein: the voltage generator adjusts an ease of occurrence of the collision induced dissociation within the first intermediate vacuum chamber by changing the DC voltage applied to one of the three elements of the ion introduction section, the ion guide and the ion transport section while maintaining the DC voltages applied to the other two elements.

8. A mass spectrometry method using a mass spectrometer including: an ionization chamber for ionizing a component in a sample in an ambience of atmosphere pressure; an analysis chamber maintained at a high degree of vacuum containing a mass spectrometry section for detecting ions after separating the ions according to their mass-to-charge ratios; one or a plurality of intermediate vacuum chambers provided between the ionization chamber and the analysis chamber; an ion introduction section with an opening for introducing ions from the ionization chamber into the subsequently located first intermediate vacuum chamber; an ion transport section having an opening for introducing ions from the first intermediate chamber into the intermediate vacuum chamber or the analysis chamber in a next stage; and an ion guide, placed within the first intermediate vacuum chamber, for creating a radio-frequency electric field for converging ions introduced through the ion introduction section to the first intermediate vacuum chamber while transporting the ions through the ion transport section to the subsequent stage, the method comprising:

applying a predetermined DC voltage to at least one of three elements of the ion introduction section, the ion guide and the ion transport section, so as to create, within the first intermediate vacuum chamber, a DC electric field which induces a dissociation of an ion due to collision induced dissociation within the first intermediate vacuum chamber, with a value of the DC voltage adjusted, using a variation in an ease of occurrence of the collision induced dissociation depending on a kind of component, so as to increase an SN ratio of a detection signal for an ion originating from a target component.

9. The mass spectrometry method according to claim 8, further comprising:

searching for an optimum voltage that is a value of the DC voltage at which a detection signal of the ion originating from the target component has an optimum or approximately optimum SN ratio.

10. The mass spectrometry method according to claim 9, wherein the searching for the optimum voltage comprises:

changing the value of the DC voltage in a stepwise manner;

acquiring a detection signal for the ion originating from the target component every time the value of the DC voltage is changed in the stepwise manner, and calculating the SN ratio of the detection signal acquired under each different value of the DC voltage, and comparing the calculated SN ratios.

11. The mass spectrometry method according to claim 8, further comprising:

storing information related to the optimum voltage in a storage section; and changing the value of the DC voltage during a measurement process for the target component in a sample so that the optimum voltage is applied to at least one of the three elements of the ion introduction section, the ion guide and the ion transport section based on the information stored in the storage section.

12. The mass spectrometry method according to claim 11, wherein the storage section holds information related to the optimum voltage for each component; further comprising
retrieving, from the storage section, a piece of information related to the optimum voltage according to a kind of the component to be analyzed, and controlling the DC voltage based on the information.

13. The mass spectrometry method according to claim 12, wherein:
the mass spectrometer is a mass spectrometer in which a sample separated into components by a column of a chromatograph is introduced into an ionization probe placed within the ionization chamber to perform a mass spectrometry; further comprising
changing the value of the DC voltage during the measurement process so as to change the optimum voltage for each component contained in the introduced sample based on the information stored in the storage section.

14. The mass spectrometry method according to claim 8, further comprising
adjusting an ease of occurrence of the collision induced dissociation within the first intermediate vacuum chamber by changing the DC voltage applied to one of the three elements of the ion introduction section, the ion guide and the ion transport section while maintaining the DC voltages applied to the other two elements.

15. The mass spectrometer according to claim 3, further comprising:
a storage section for storing information related to the optimum voltage obtained by the optimum voltage searcher; and
a measurement process controller for controlling the voltage generator during a measurement process for the target component in a sample so that the optimum voltage is applied to at least one of the three elements of the ion introduction section, the ion guide and the ion transport section based on the information stored in the storage section.

16. The mass spectrometer according to claim 15, wherein:
the storage section holds information related to the optimum voltage for each component; and
the measurement process controller retrieves, from the storage section, a piece of information related to the optimum voltage according to a kind of the component to be analyzed, and controls the voltage generator based on the information.

17. The mass spectrometer according to claim 16, wherein:
the mass spectrometer is a mass spectrometer in which a sample separated into components by a column of a chromatograph is introduced into an ionization probe placed within the ionization chamber to perform a mass spectrometry; and
the measurement process controller controls the voltage generator during the measurement process so as to change the optimum voltage for each component contained in the introduced sample based on the information stored in the storage section.

18. The mass spectrometer according to claim 2, wherein:
the voltage generator adjusts an ease of occurrence of the collision induced dissociation within the first intermediate vacuum chamber by changing the DC voltage applied to one of the three elements of the ion introduction section, the ion guide and the ion transport section while maintaining the DC voltages applied to the other two elements.

19. The mass spectrometer according to claim 3, wherein:
the voltage generator adjusts an ease of occurrence of the collision induced dissociation within the first intermediate vacuum chamber by changing the DC voltage applied to one of the three elements of the ion introduction section, the ion guide and the ion transport section while maintaining the DC voltages applied to the other two elements.

20. The mass spectrometer according to claim 4, wherein:
the voltage generator adjusts an ease of occurrence of the collision induced dissociation within the first intermediate vacuum chamber by changing the DC voltage applied to one of the three elements of the ion introduction section, the ion guide and the ion transport section while maintaining the DC voltages applied to the other two elements.

21. The mass spectrometer according to claim 5, wherein:
the voltage generator adjusts an ease of occurrence of the collision induced dissociation within the first intermediate vacuum chamber by changing the DC voltage applied to one of the three elements of the ion introduction section, the ion guide and the ion transport section while maintaining the DC voltages applied to the other two elements.

22. The mass spectrometer according to claim 6, wherein:
the voltage generator adjusts an ease of occurrence of the collision induced dissociation within the first intermediate vacuum chamber by changing the DC voltage applied to one of the three elements of the ion introduction section, the ion guide and the ion transport section while maintaining the DC voltages applied to the other two elements.

* * * * *